United States Patent
Hashimoto et al.

(10) Patent No.: US 8,532,250 B2
(45) Date of Patent: Sep. 10, 2013

(54) X-RAY CT APPARATUS AND CONTROL METHOD FOR X-RAY CT APPARATUS

(75) Inventors: Atsushi Hashimoto, Yaita (JP); Takayuki Yamazaki, Nasushiobara (JP); Michito Nakayama, Utsunomiya (JP); Tomoe Sagoh, Utsunomiya (JP); Takeshi Miyagi, Fujisawa (JP)

(73) Assignees: Kabushiki Kaisha Toshiba, Tokyo (JP); Toshiba Medical Systems Corporation, Tochigi-Ken (JP)

(*) Notice: Subject to any disclaimer, the term of this patent is extended or adjusted under 35 U.S.C. 154(b) by 401 days.

(21) Appl. No.: 13/031,859

(22) Filed: Feb. 22, 2011

(65) Prior Publication Data

US 2011/0222649 A1 Sep. 15, 2011

(30) Foreign Application Priority Data

Feb. 24, 2010 (JP) ................................. 2010-038809

(51) Int. Cl.
  *G01N 23/083* (2006.01)
  *H05G 1/64* (2006.01)
  *H05G 1/54* (2006.01)
  *G01T 1/24* (2006.01)

(52) U.S. Cl.
  USPC ........ 378/19; 378/98.8; 378/117; 250/370.15

(58) Field of Classification Search
  USPC ...................... 378/19, 98.8, 117; 250/370.15
  See application file for complete search history.

(56) References Cited

U.S. PATENT DOCUMENTS

| | | | |
|---|---|---|---|
| 5,103,092 A * | 4/1992 | Takahashi et al. | 250/252.1 |
| 6,198,791 B1 * | 3/2001 | He et al. | 378/19 |
| 7,078,703 B2 * | 7/2006 | Watanabe | 250/370.15 |
| 7,135,687 B2 * | 11/2006 | Lacey et al. | 250/370.15 |
| 2003/0016779 A1 * | 1/2003 | Pohan et al. | 378/19 |
| 2008/0069296 A1 * | 3/2008 | Joshi et al. | 378/19 |
| 2009/0014661 A1 * | 1/2009 | Yagi et al. | 250/370.11 |

FOREIGN PATENT DOCUMENTS

JP 2001-215281 A 8/2001

* cited by examiner

*Primary Examiner* — Thomas R Artman
(74) *Attorney, Agent, or Firm* — Yoshida&Associates, LLC

(57) ABSTRACT

An X-ray CT apparatus has an X-ray source, an X-ray detector, a temperature sensor, a data acquisition unit and a controller. The X-ray source generates an X-ray. The X-ray detector detects the X-ray. The temperature sensor detects a temperature of the X-ray detector. The data acquisition unit acquires data from the X-ray detector. The controller controls a temperature of the X-ray detector through adjustment of a workload of the data acquisition unit during a non-scanning time.

13 Claims, 9 Drawing Sheets

X-RAY CT APPARATUS AND CONTROL METHOD FOR X-RAY CT APPARATUS

CROSS-REFERENCE TO RELATED APPLICATION

This application is based upon and claims the benefit of priority from Japanese Patent Application No. 2010-38809, filed on Feb. 24, 2010, the entire contents of which are incorporated herein by reference.

FIELD

The present embodiments relates to an X-ray CT apparatus and a control method for the X-ray CT apparatus including an X-ray detector and a data acquisition system (DAS), in which the temperature of a detection element that makes up the X-ray detector is controlled.

BACKGROUND

An X-ray CT apparatus includes an X-ray source and an X-ray detector, which are disposed interposing an object in an opposing manner. The X-ray detector includes multiple channels (M channels) of detection elements along a direction orthogonal to the longitudinal direction of a table-top, which is the direction of the body axis of the object.

While various types of X-ray detectors are available, a scintillation detector, which has potential for downsizing, is generally used for X-ray CT apparatuses. Each detection element of the scintillation detector includes a scintillator and a photosensor, such as a photodiode (PD). The scintillator absorbs X-rays that are collimated in a preceding stage, and generates fluorescence through the absorption. The PD converts the fluorescence into an electric signal and outputs the electric signal to a data acquisition system (DAS). That is, according to an X-ray CT apparatus, an X-ray beam is delivered in a fan shape to a section (hereafter, referred to as a "slice plane") of the object from the X-ray source so that X-ray beams that have transmitted a certain slice plane of the object are converted into an electric signal for every detection element of the X-ray detector thereby allowing the acquisition of transmission data.

Further, compared to the above described single-slice X-ray CT apparatus, a multi-slice X-ray CT apparatus includes, besides M channels of detection elements, a multiple rows (N rows) of detection elements along the body axis of the object, in the X-ray detector. The X-ray detector of the multi-slice X-ray CT apparatus is configured as a two-dimensional detector for X-ray CT having M channels×N rows of detection elements in total.

FIG. 9 is a side view showing an outline of the configuration of the periphery of an X-ray detector and a DAS in a conventional X-ray CT apparatus.

FIG. 9 shows an X-ray detector (a scintillation detector) 61, a DAS 62, a thermal shield 63 and a heater 64 which are disposed between the X-ray detector 61 and the DAS 62, and cooling fans 65a and 65b which are disposed in the periphery of the X-ray detector 61 and the DAS 62, in a conventional X-ray CT apparatus. As shown in FIG. 9, the X-ray detector 61 includes a collimator (N collimators corresponding to N rows) 71 which collimates the X ray that has transmitted an object, a detection element (N detection elements corresponding to N rows) 72 which generates an electric signal based on the X ray in a subsequent stage of the collimator 71. The detection element 72 is made up of a scintillator (N scintillators) 81 and a PD (a photodiode array (PDA) having N PDs) 82. The DAS 62, which is disposed in a subsequent stage of the PD 82, converts and amplifies the electric signal of the PD 82 into a voltage signal.

The collimator 71 and the detection element 72, which make up the X-ray detector 51, are configured as one body and are thermally shielded from the DAS 62, in which temperature significantly fluctuates, via a thermal shield 63 to keep the detection element 72, particularly the PD 82, at a constant temperature. Alternatively, the collimator 71 and the detection element 72 are configured as one body and are accommodated in a case as the thermal shield 63 to keep the detection element 72 at a constant temperature. Then, temperature control of the detection element 72 is performed by heating the detection element 72, which has no effect on the temperature fluctuation of the DAS 62, with the heater 64 of about 100 to about 150 [W] and also cooling the detection element 72 with the cooling fan 65a. The temperature of the detection element 72 is controlled, for example, in a range of 40±1 [° C.] which is higher than the room temperature, with the heater 64 and the cooling fan 65a. It is possible to maintain the image quality of CT images by controlling the temperature of the detection element 72.

On the other hand, in some cases, the substrate temperature of the DAS 62 rises to about 60 to about 90 [° C.] due to generated heat, leading to a malfunction of the DAS 62. In order to prevent an excessive temperature rise of the DAS 62, a cooling fan 65b for cooling the DAS 62 is attached to the substrate of the DAS 62. Thus, it is configured such that there is no excessive temperature rise in the DAS 62.

As so far described, in order to control the temperature of the X-ray detector 50, while the thermal shield 63 is used to shield exhaust heat of the DAS 62, heating equipment is provided on the side of the detection element 72 and, at the same time, cooling equipment is provided on the side of the DAS 62.

Thus, the conventional X-ray CT apparatus causes a waste of electric power in that, on one hand, heating of the detection element is performed while shielding exhaust heat of the DAS and, on the other hand, cooling of the detection element is performed in order to control the temperature of the detection element of the X-ray detector.

Moreover, as the DAS becomes more highly integrated and thereby downsized in recent years, it is required from a viewpoint of performance enhancement that the X-ray detector and the DAS are installed adjacent to each other. As an extreme of this configuration, it is conceivable that the X-ray detector and the DAS are configured to be a unitary structure (a modular structure). However, if a thermal shield is not installed in the conventional X-ray CT apparatus, the exhaust heat of the DAS will directly affect the temperature of the detection element making it difficult to keep the detection element at a constant temperature. Thus, since installing a thermal shield is a necessity in the conventional X-ray CT apparatus, it is difficult to achieve a unitary structure of the X-ray detector and the DAS. Further, if no heater is installed in the conventional X-ray CT apparatus, it cannot be expected that the temperature of the detection element is hematothermal. Thus, since installing a heater is a necessity in a conventional X-ray CT apparatus, it is difficult to achieve a unitary structure of the X-ray detector and the DAS.

In addition, disposing a heater in the vicinity of the X-ray detector may result in an ill effect that the heater acts as a noise source.

BRIEF DESCRIPTION OF THE DRAWINGS

In accompanying drawings.

DETAILED DESCRIPTION

An X-ray CT apparatus and a control method for the X-ray CT apparatus of the present embodiment will be described with reference to appended drawings.

To solve the above-described problems, the X-ray CT apparatus according to the present embodiment has: an X-ray source configured to generate an X-ray; an X-ray detector configured to detect the X-ray; a temperature sensor configured to detect a temperature of the X-ray detector; a data acquisition unit configured to acquire data from the X-ray detector; and a controller configured to control a temperature of the X-ray detector through adjustment, of a workload of the data acquisition unit during a non-scanning time.

To solve the above-described problems, a control method for the X-ray CT apparatus according to the present embodiment, which has: an X-ray source configured to generate an X-ray; an X-ray detector configured to detect the X-ray; a temperature sensor configured to detect a temperature of the X-ray detector; and a data acquisition unit configured to acquire data from the X-ray detector, comprising: a controlling step that controls a temperature of the X-ray detector through adjustment of a workload of the data acquisition unit during a non-scanning time.

There are various types of X-ray CT apparatuses of the present embodiment, such as a ROTATE/ROTATE type in which an X-ray tube and an X-ray detector rotate as one body around an object, a STATIONARY/ROTATE type in which a large number of detection elements are arrayed in a ring-shape, and only the X-ray tube rotates around the object, and the like. The present invention can be applied to any of those types. Hereafter, the ROTATE/ROTATE type which is currently in a mainstream position will be described.

Further, the current mainstream of the mechanism for converting incoming X-ray into electric charge includes an indirect conversion type in which X-ray is converted into light with a fluorescent body such as a scintillator, etc., and the light is converted into electric charge with a photoelectric conversion element such as a photodiode, etc., and a direct conversion type in which the generation of an electron-hole pair in a semiconductor and the transfer thereof to an electrode, that is, a photoconductive phenomenon is utilized.

In addition, in recent years, a progress has been made in the commercialization of a so-called multi-tube type X-ray CT apparatus, in which a plurality of pairs of the X-ray tube and the X-ray detector are mounted on a rotary ring, and the development of peripheral technologies thereof has been in progress. The X-ray CT apparatus of the present embodiment can be applied to either of a conventional single-tube type X-ray CT apparatus, or a multi-tube type X-ray CT apparatus. Here, description will be made supposing a single-tube type X-ray CT apparatus.

(First Embodiment)

Figure 1:
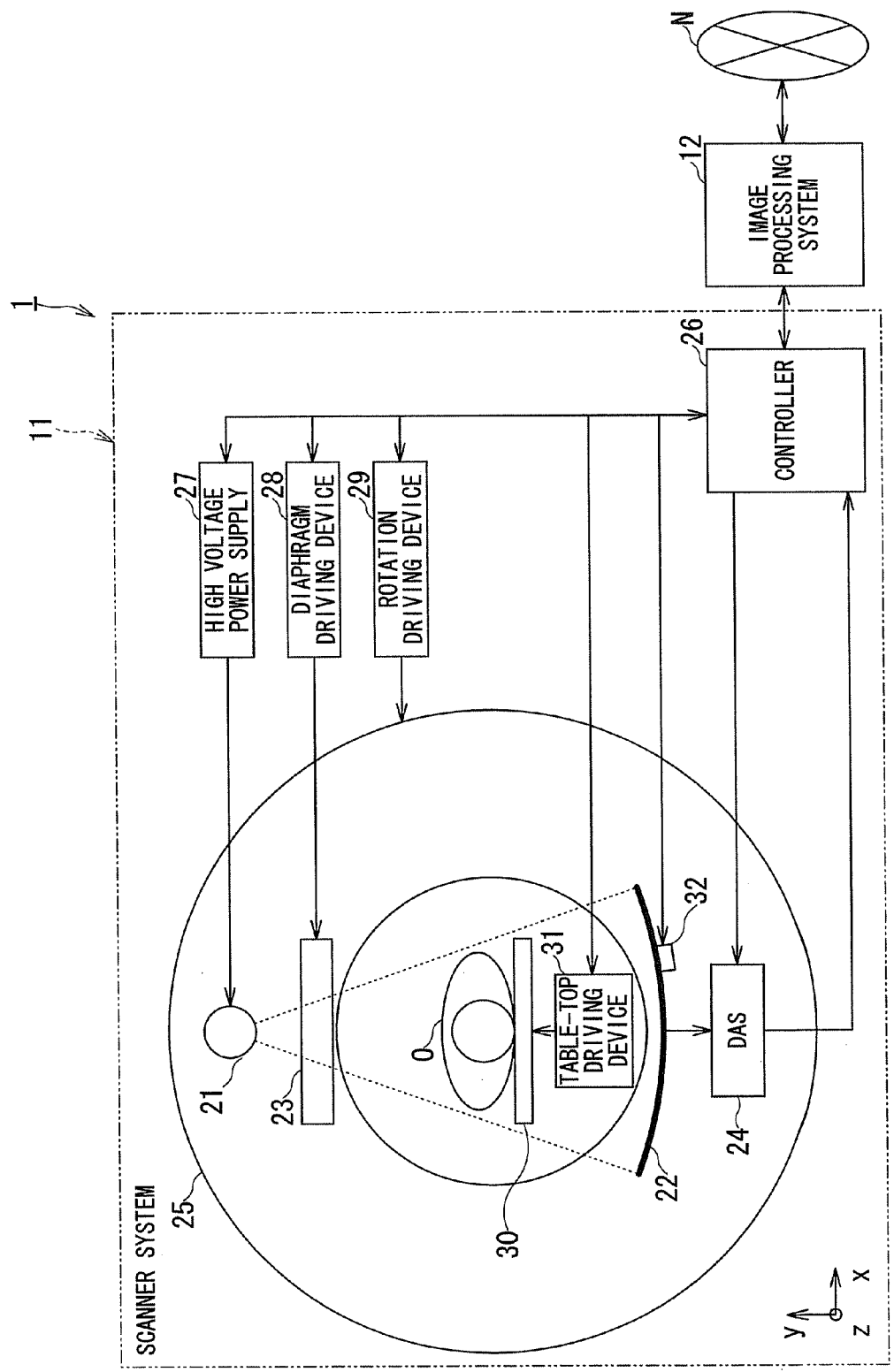
FIG. 1 is a hardware configuration diagram showing an X-ray CT apparatus of a first embodiment.

FIG. 1 is a hardware configuration diagram showing an X-ray CT apparatus of a first embodiment.

FIG. 1 shows an X-ray CT apparatus 1 of the first embodiment. The X-ray CT apparatus 1 is broadly made up of a scanner system 11 and an image processing system 12. The scanner system 11 of the X-ray CT apparatus 1 is generally installed in an examination room, and is configured to generate transmission data of the X-ray relating to an exposure region of an object (human body) O. On the other hand, the image processing system 12 is generally installed in a control room adjacent to an examination room, and is configured to generate projection data based on the transmission data and to generate and display a reconstructed image.

The scanner system 11 of the X-ray CT apparatus 1 has an X-ray tube 21 as an X-ray source, an X-ray detector (a scintillation detector) 22, a diaphragm (collimator) 23, a DAS (data acquisition system) 24, a rotating portion 25, a controller 26, a high voltage power supply 27, a diaphragm driving device 28, a rotation driving device 29, a table-top 30, a table-top driving device (a bed system) 31 and a temperature sensor 32.

The X-ray tube 21 delivers X-ray toward the X-ray detector 22 according to the tube voltage supplied from the high voltage power supply 27. The X-ray delivered from the X-ray tube 21 forms a fan-beam X-ray and a cone-beam X-ray.

The X-ray detector 22 is an X-ray detector of one-dimensional array type which has multiple (M) channels in a direction (channel direction) orthogonal to a longitudinal direction of the table-top, which is the body axis direction, and one row of detection elements in a slice direction (row direction). Alternatively, the X-ray detector 22 is an X-ray detector of two-dimensional array type (also referred to as a multi-slice type detector) which has detection elements of matrix form, that is, M channels and multiple (N) rows in the slice direction. Hereafter, description will be made on a case in which the X-ray detector 22 is an X-ray detector of two-dimensional array type. The X-ray detector 22 detects X-ray that is delivered from the X-ray tube 21 and has transmitted through the object O.

The diaphragm 23 is adapted to adjust a range to be irradiated in the slice direction with X-ray delivered from the X-ray tube 21. That is, it is possible to vary the range to be irradiated with X-ray in the slice direction by adjusting the opening of the diaphragm 23 with the diaphragm driving device 28.

The DAS 24 converts and amplifies an electric signal of the transmission data detected by each detection element of the X-ray detector 22 into a voltage signal, and further converts it into a digital signal. The output data of the DAS 24 is provided to the image processing system 12.

The rotating portion 25 is accommodated in a gantry (not shown) of the scanner system 11, and holds the X-ray tube 21, the X-ray detector 22, the diaphragm 23, and the DAS 24 in one body. The rotating portion 25 is configured so as to be able to rotate the X-ray tube 21, the X-ray detector 22, the diaphragm 23, and the DAS 24 in one body around the object O, with the X-ray tube 21 and the X-ray detector 22 being opposed to each other.

The controller 26 is made up of a CPU (central processing unit) and a memory. The controller 26 controls the DAS 24, the high-voltage power supply 27, the diaphragm driving device 28, the rotation driving device 29, the table-top driving device 31, and the temperature sensor 32, etc. based on a control signal inputted from the image processing system 12 such that scanning is executed.

The high-voltage power supply 27 supplies power needed for irradiation of X-ray, to the X-ray tube 21 through the control by the controller 26.

The diaphragm driving device 28 adjusts the irradiation range in the slice direction of X-ray at the diaphragm 23 through the control by the controller 26.

The rotation driving device 29 rotates the rotating portion 25 such that the rotating portion 25 rotates around a cavity portion with the positional relationship therebetween being maintained, through the control by the controller 26.

The table-top 30 can carry the object O.

The table-top driving device 31 moves the table-top 30 along the z-axis direction through the control by the controller 26. The central portion of the rotating portion 25 has an opening, and the object O placed on the table-top 30 is inserted through the opening.

The temperature sensor 32 is attached to a detection element unit 42 (shown in FIG. 2) of the X-ray detector 22. The temperature sensor 32 transmits the temperature information, which is repeatedly detected, of the detection element unit 42, particularly the photodiode array (PDA) 52 (shown in FIG. 2) to the controller 26. It is noted that the temperature sensor 32 may be a temperature sensing circuit which is fabricated in a semiconductor process and is to be embedded in the PDA 52. In that case, for example, the temperature sensor 32 is a CMOS temperature sensor circuit which is fabricated in the CMOS (complementary metal oxide semiconductor) process and to be embedded in the PDA 52.

The image processing system 12 of the X-ray CT apparatus 1 is made up based on a computer, and can perform two-way communication with a network N such as a LAN (local area network) of hospital backbone network. The image processing system 12 is made up of basic hardware such as, although not shown, a CPU, a memory, an HDD (hard disc drive), an input device and a display device, etc.

The image processing system 12 generates projection data by performing correction processing (preprocessing) such as logarithmic conversion processing, sensitivity correction, and the like on the raw data inputted from the DAS 24 of the scanner system 11. Moreover, the image processing system 12 performs eliminating processing of scattered rays on the preprocessed projection data. The image processing system 12, which is supposed to perform the elimination of scattered rays based on the value of the projection data within a range to be irradiated with X-ray, performs scattered ray correction by subtracting scattered rays estimated from the magnitude of the value of the target projection data to be subjected to scattered ray correction, or the adjacent projection data thereof, from target projection data. The image processing system 12 generates a reconstructed image based on the corrected projection data.

Figure 2:
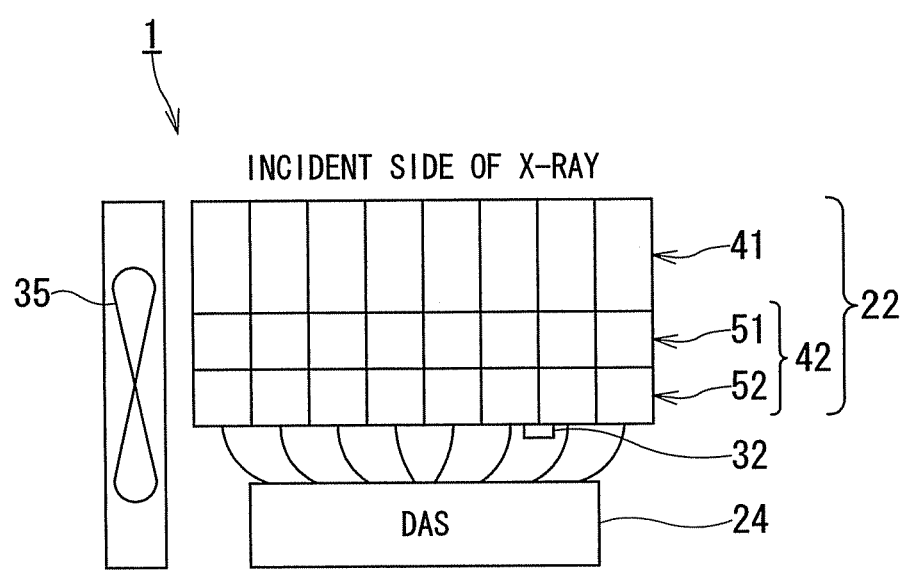
FIG. 2 is a side view showing an outline of a configuration of the periphery of an X-ray detector and a DAS in the X-ray CT apparatus of the first embodiment.

FIG. 2 is a side view showing an outline of the configuration of the periphery of the X-ray detector 22 and the DAS 24 in the X-ray CT apparatus of the first embodiment.

FIG. 2 shows an X-ray detector 22, a DAS 24, and a cooling fan 35 which is disposed in the periphery of the X-ray detector 22 and the DAS 24. The X-ray detector 22 includes a collimator (a collimator unit having M×N collimators) 41 that collimates X-ray that has transmitted an object O, and a detection element (a detection element unit having M×N detection elements) 42 that generates an electric signal based on the X-ray in a subsequent stage of the collimator unit 41. The detection element unit 42 is made up of a scintillator (a scintillator unit having M×N scintillators) 51, and a PD (a PDA having M×N PDs) 52. It is noted that FIG. 2 shows, for example, a collimator unit 41 based on 8 collimators corresponding to 8 (N=8) rows of required channels, a scintillator unit 51 based on 8 scintillators corresponding to (N=8) rows of required channels, and a PDA 52 based on 8 PDs corresponding to 8 rows of required channels.

The DAS 24 is disposed in a subsequent stage of the PDA 52 such that the output surface of the X-ray detector 22 and the input surface of the DAS 24 are opposed to each other. It is noted that when, although not shown, the temperature sensor 32 is a temperature sensor circuit which is fabricated in the semiconductor process and to be embedded in the PDA 52, it is possible to configure the DAS 24 and the X-ray detector 22 to be a unitary structure (a modular structure). The DAS 24 converts and amplifies an electric signal from the PDA 52 into a voltage signal, and further converts it into a digital signal.

The cooling fan 35 is attached to a substrate (not shown) of the DAS 24 to cool the DAS 24 (and the X-ray detector 22).

Moreover, as shown in FIG. 2, one temperature sensor 32 (or a plurality of temperature sensors) is attached to the DAS 24 side of the PDA 52 of the detection element unit 42 so that the controller 26 controls the temperature of the detection element unit 42 through feedback control. The controller 26 adjusts the workload of the chip mounted in the DAS 24 when raising the temperature of the detection element unit 42. On the other hand, the controller 26 adjusts the workload of the chip mounted in the DAS 24 or/and the volume of air of the cooling fan 35 when lowering the temperature of the detection element unit 42. The adjustment of the workload of the chip is implemented by adjusting the number of the chips that perform acquisition operation (calculation processing), the operation interval of the chip that discretely performs acquisition operation, or the rate of the acquisition operation. In this way, the temperature of the detection element unit 42 of the X-ray detector 22 is controlled within a range of, for example, about 40±1 [° C.] which is higher than the room temperature by the adjustments of the workload of the chip mounted on the DAS 24 and the amount of air of the cooling fan 35. It is possible to maintain the image quality of the CT image that is generated by the image processing system 12 by controlling the temperature of the detection element unit 42.

Figure 3:
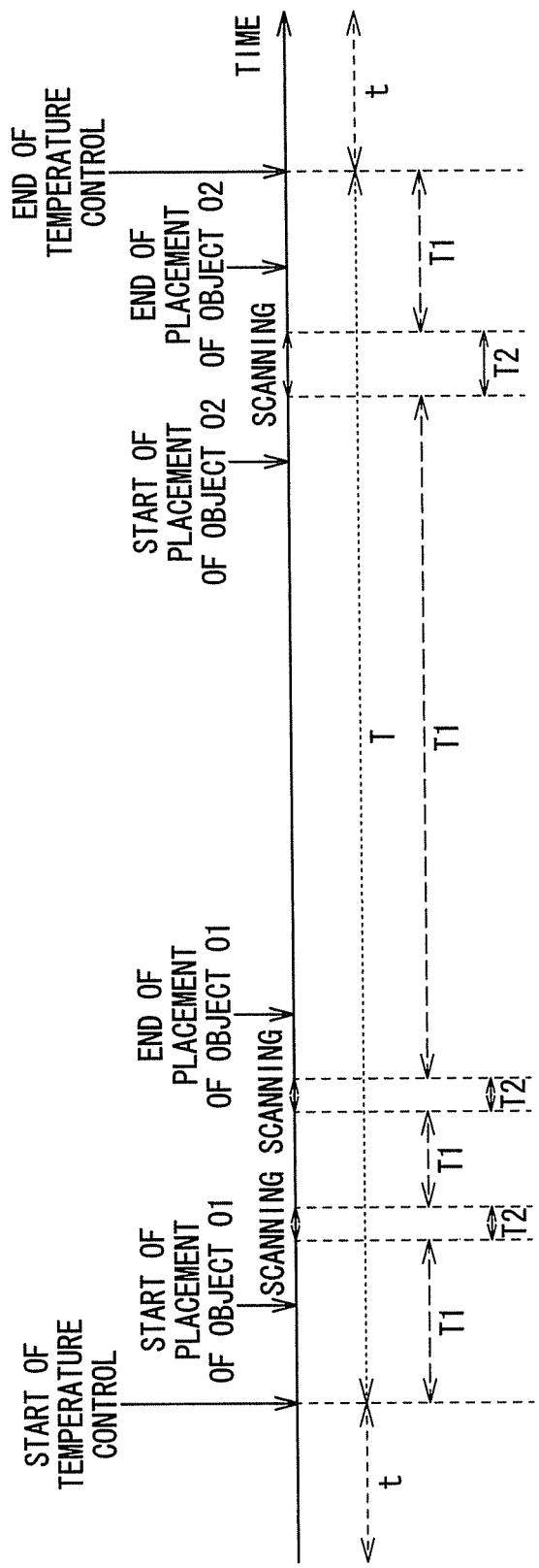
FIG. 3 is a diagram showing an example of a time chart to illustrate an operation of the X-ray CT apparatus of the first embodiment and a second embodiment.

FIG. 3 is a diagram showing an example of the time chart to illustrate the operation of an X-ray CT apparatus of the first embodiment.

As shown in FIG. 3, the X-ray CT apparatus 1 performs two scanning operations (for example, conventional scanning) after starting the placement of an object O1 on a table-top 30, thereafter ending the placement of the object O1. Successively, the X-ray CT apparatus 1 performs one scanning operation (for example, helical scanning) after starting the placement of an object O2 on the table-top 30, thereafter ending the placement of the object O2. The X-ray CT apparatus 1 ends the operation after the scanning of the object O2.

In a temperature non-controlled period t shown in FIG. 3, since the controller 26 does not control the temperature of the detection element unit 42 and no scanning is executed as well, the temperature of the room in which the X-ray CT apparatus is installed becomes a major disturbance, and the temperature of the detection element unit 42 converges to the room temperature.

The period other than the temperature non-controlled period t is a temperature controlled period T. In a non-scanning period (scanning standby period) T1 which is in a temperature controlled period T, the temperature of the room in which the X-ray CT apparatus is installed becomes a major disturbance so that the temperature of the detection element unit 42 converges to the room temperature. Accordingly, in the non-scanning period T1, the controller 26 performs a feedback control of the temperature of the detection element unit 42, which is repeatedly detected by the temperature sensor 32, as the controlled object with an appropriate temperature of the detection element unit 42 as the target value and with the amount of exhaust heat of the DAS 24 as the manipulated variable. For example, the controller 26 performs a PID control of the temperature of the detection element unit 42. Since the amount of the exhaust heat of the DAS 24 is proportional to the workload of the chip mounted on the DAS 24, that is, the power consumption of the mounted chip, the controller 26 controls the temperature of the detection element unit 42 through adjustment of the workload of the chip.

On the other hand, in a scanning period T2 which is in a temperature controlled period T, the exhaust heat of the DAS 24 becomes a major disturbance, and the temperature of the detection element unit 42 rises. In the scanning period T2, the controller 26 performs a feedback control of the temperature of the detection element unit 42, which is repeatedly detected by the temperature sensor 32, as a controlled object with an appropriate temperature of the detection element unit 42 as the target value and with the amount of air of the cooling fan 35 as the manipulated variable. For example, the controller 26 performs a PID control of the temperature of the detection element unit 42.

Figure 4:
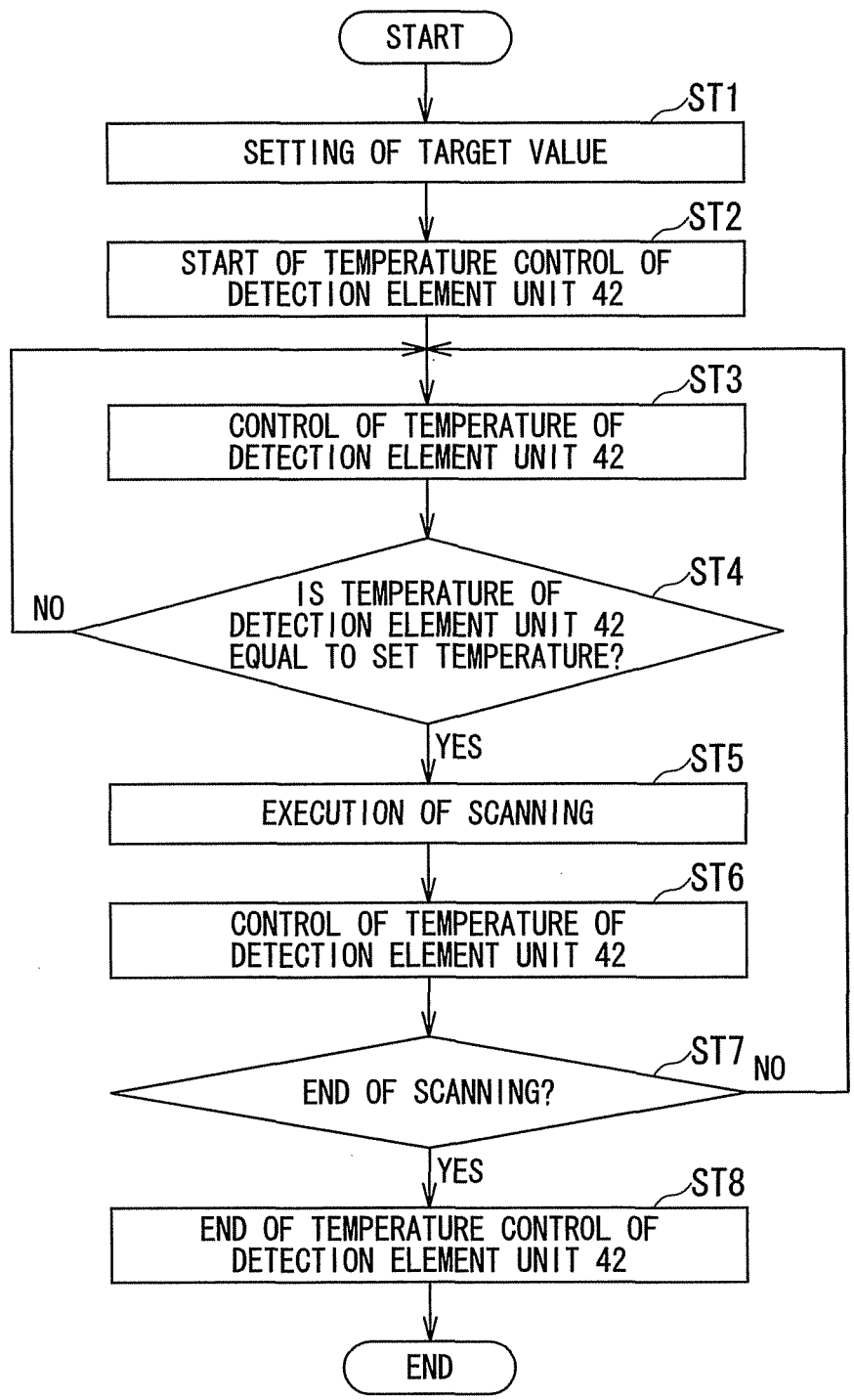
FIG. 4 is a flowchart showing the operation of the X-ray CT apparatus of the first embodiment.

Next, the operation of the X-ray CT apparatus 1 of the first embodiment will be described by using a flowchart shown in FIG. 4.

First, the controller 26 of the X-ray CT apparatus 1 sets an appropriate temperature of the detection element unit 42, particularly the PDA 52 of the X-ray detector 22, as a target value (step ST1). When an operator inputs, for example, a range of 40±1 [° C.] through an input device (not shown) of the image processing system 12, the controller 26 sets the range of 40±1 [° C.] as the target value.

Next, upon input by the operator through the input device (not shown) of the image processing system 12, the controller starts the control of the temperature of the detection element unit 42 (step ST2). When the temperature control of the detection element unit 42 is started at step ST2, the X-ray CT apparatus 1 comes into a standby state waiting for scanning. That is, using FIG. 3, the X-ray CT apparatus 1 makes a transition from a temperature non-control period t to a non-scanning period T1 which is a temperature controlled period T.

In the non-scanning period T1, the controller 26 repeatedly detects the temperature of the detection element unit 42 with the temperature sensor 32. Then, the controller 26 adjusts the acquisition operation of the DAS 24 between from 0 to a maximum based on the temperature of the detection element unit 42, with an appropriate temperature set at step ST1 as the target value, thereby adjusting the power consumption of the DAS 24. That is, the controller 26 controls the temperature of the detection element unit 42 (step ST3). For example, in step ST3, a PID control of the temperature of the detection element unit 42 is performed with the power consumption of the DAS 24 as the manipulated variable.

Next, upon receiving an instruction to start scanning, the controller 26 determines whether or not the temperature of the detection element unit 42 detected by the temperature sensor 32 is equal to the target value set at step ST1 (step ST4). When the determination at step ST4 is YES, that is, it is determined that the temperature of the detection element unit 42 detected by the temperature sensor 32 is equal to the target value set at step ST1, the controller 26 executes scanning (step ST5). That is, using FIG. 3, the X-ray CT apparatus 1 makes a transition from a non-scanning period T1 to a scanning period T2.

In the scanning period T2, the controller 26 repeatedly detects the temperature of the detection element unit 42 with the temperature sensor 32. Then, the controller 26 adjusts the amount of air of the cooling fan 35 based on the temperature of the detection element unit 42, which are repeatedly detected with the temperature sensor 32, with the appropriate temperature set at step ST1 as the target value. That is, the controller 26 controls the temperature of the detection element unit 42 (step ST6). For example, in step ST6, a PID control of the temperature of the detection element unit 42 is performed with the amount of air of the cooling fan 35 as the manipulated variable.

On the other hand, when the determination at step ST4 is NO, that is, it is determined that the temperature of the detection element unit 42 detected with the temperature sensor is not equal to the target value set at step ST1, the controller 26 controls the temperature of the detection element unit 42 until the temperature of the detection element unit 42 reaches the target value set at step ST1 (step ST3).

The controller 26 determines whether or not to end the control of the temperature of the detection element unit 42 (step ST7). When the determination at step ST7 is YES, that is, it is determined to end the control of the temperature of the detection element unit 42, the controller 26 ends the operation (step ST8). That is, using FIG. 3, the X-ray CT apparatus 1 makes a transition from a scanning period T2 to a temperature non-controlled period t. For example, when all the scanning to be performed in a certain day is finished, and an operator inputs an instruction to end the process through an input device (not shown) of the image processing system 12, the controller 26 determines to end the control of the temperature of the detection element unit 42.

On the other hand, when the determination at step ST7 is NO, that is, it is determined not to end the control of the temperature of the detection element unit 42, that is, to continue the scanning, the controller 26 controls the temperature of the detection element unit 42 (step ST3). That is, using FIG. 3, the X-ray CT apparatus 1 makes a transition from a scanning period T2 to a non-scanning period T1.

According to the X-ray CT apparatus 1 of the first embodiment, it is possible to facilitate the temperature control of the detection element unit 42 with a simple structure in which no heater is used, thereby improving the image quality of a CT image, and allowing the temperature control to be applied particularly to a case in which the X-ray detector 22 and the DAS 24 are configured to be adjacent structures, or a unitary structure.

It is noted that even in the X-ray CT apparatus 1, a plurality of temperature sensors 32 may be provided in a plane direction as will be described using an X-ray CT apparatus 1A of a second embodiment. In such a case, it is possible to adjust temperature for every detection element of the detection element unit 42 by respectively adjusting the workloads of the plurality of chips mounted on the DAS 24 according to the temperature distribution of the detection element unit 42.

(Second Embodiment)

Figure 5:
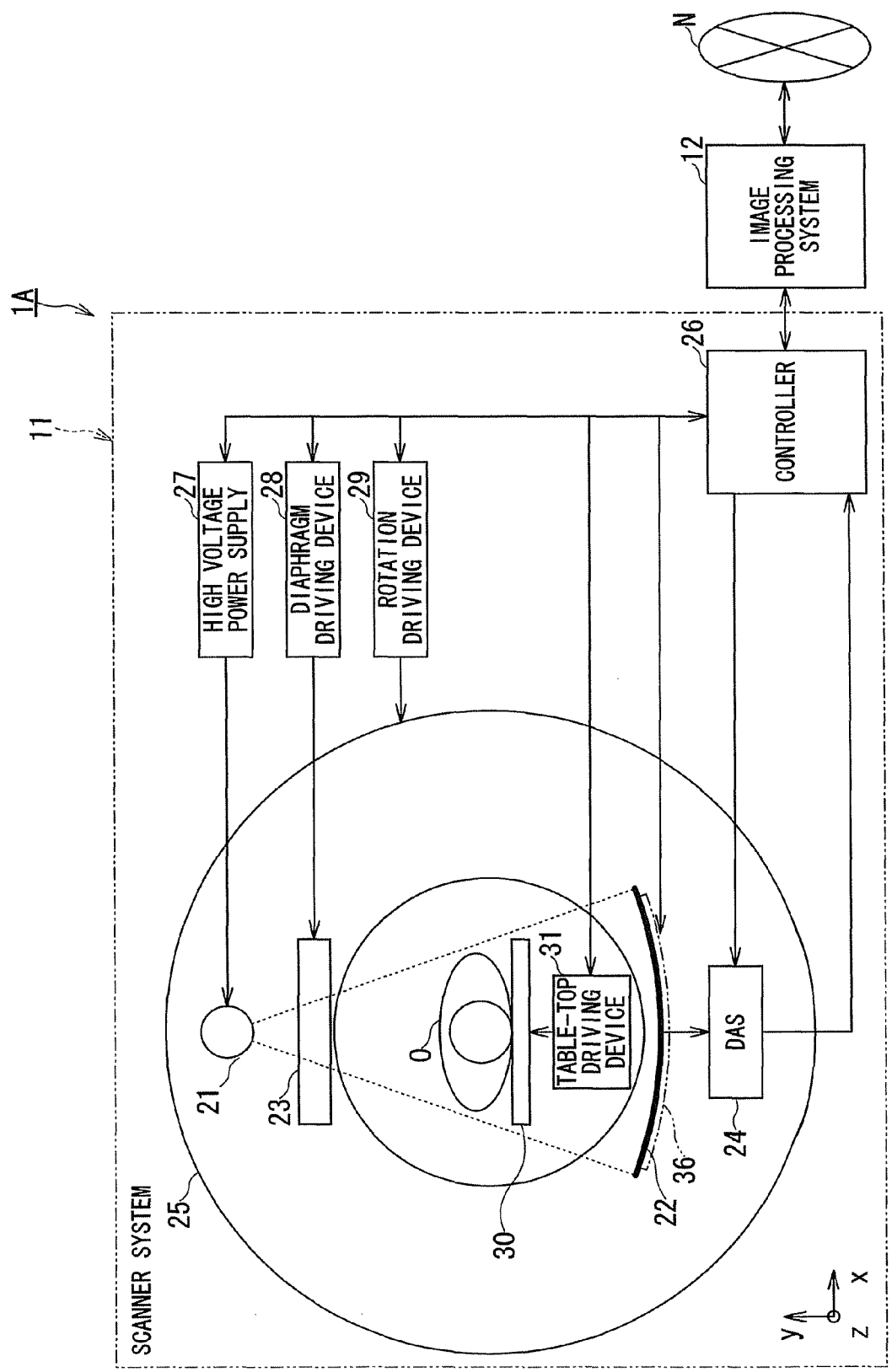
FIG. 5 is a hardware configuration diagram showing an X-ray CT apparatus of a second embodiment.

FIG. 5 is a hardware configuration diagram showing an X-ray CT apparatus of a second embodiment.

FIG. 5 shows an X-ray CT apparatus 1A of the second embodiment. The X-ray CT apparatus 1A is broadly made up of a scanner system 11 and an image processing system 12. It is noted that in the X-ray CT apparatus 1A shown in FIG. 5, the same components as those of the X-ray CT apparatus 1 shown in FIG. 1 are given the same reference characters, and their description will be omitted.

The X-ray CT apparatus 1 of the first embodiment is configured such that the workload of the DAS 24 is adjusted to heat the detection element unit 42 without the need of a heater, thereby making it possible to configure the X-ray detector 22 and the DAS 24 to be adjacent structures, or a unitary structure. On the other hand, the X-ray CT apparatus 1A of the second embodiment is configured such that the workload of the DAS 24 and the capacity of the heater are adjusted to heat the detection element unit 42 while reducing the size of the heater, thereby making it possible to configure the X-ray detector 22 and the DAS 24 to be adjacent structures, or a unitary structure.

The scanner system 11 of the X-ray CT apparatus 1A includes a heater unit 36 which is attached to the DAS 24 side of the X-ray detector 22.

Figure 6:
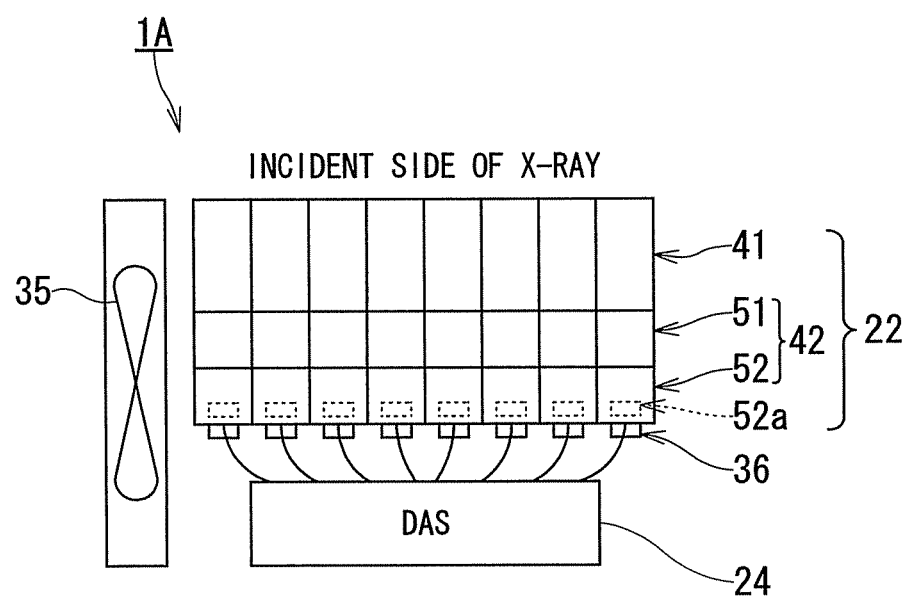
FIG. 6 is a side view showing an outline of a configuration of the periphery of an X-ray detector and a DAS in the X-ray CT apparatus of the second embodiment.

FIG. 6 is a side view showing an outline of the configuration of the periphery of the X-ray detector 22 and the DAS 24 in the X-ray CT apparatus of the second embodiment.

FIG. 6 shows the X-ray detector 22, the DAS 24, a cooling fan 35 which is disposed in the periphery of the X-ray detector 22 and the DAS 24, and a heater (a heater unit having a plurality of heaters) 36 which is attached to the DAS 24 side of the X-ray detector 22. It is noted that FIG. 6 shows a heater unit 36 made up of 8 heaters corresponding to 8 rows of the required channels.

In the X-ray CT apparatus 1A shown in FIG. 6, the same components as those of the X-ray CT apparatus 1 shown in FIG. 2 are given the same reference characters, and their description will be omitted.

The PDA 52 is configured such that a temperature sensor as a temperature sensor circuit that is fabricated by the semiconductor process is embedded in each of the plurality (all) of PDs that make up the PDA 52. FIG. 6 shows, for example, a temperature sensor unit 52a made up of 8 temperature sensors corresponding to 8 rows of the required channels. It is noted that a plurality of temperature sensors may be attached to the DAS 24 side of the PDA 52, as the substitute for the temperature sensor unit 52a. In the case of such configuration, it is possible to measure a temperature distribution of the detection element unit 42. Moreover, although the temperature distribution of the detection element unit 42 cannot be measured, a temperature sensor as a temperature sensor circuit fabricated by a semiconductor process may be embedded in only one PD that makes up the PDA 52, or one temperature sensor may be attached to the DAS 24 side of the PDA 52 as shown in FIG. 2.

The heater unit 36 is attached to the DAS 24 side of the plurality (all) of PDs that make up the PDA 52. In such a case, since the capacity (power) of every heater that makes up the heater unit 36 can be controlled, the temperature of every detection element of the detection element unit 42 can be controlled. Since the exhaust heat of the DAS 24 besides the heater unit 36 is utilized to heat the detection element unit 42 in the X-ray CT apparatus 1A, it is possible to make the heater unit 36 more compact compared to conventional heaters. Therefore, it is possible to arrange the X-ray detector 22 and the DAS 24 closer to each other. In addition, although not shown, attaching the heater of the heater unit 36 to a place other than the DAS 24 side of the PDA 52, for example, a reflector of the PDA 52 will make it possible to configure the X-ray detector 22 and the DAS 24 to be a unitary structure.

The controller 26 performs temperature control by feedback control for every detection element of the detection element unit 42. When raising the temperature of a certain detection element of the detection element unit 42, the controller 26 adjusts the workload of the chip which is mounted on the DAS 24 and located in the vicinity of the concerned detection element, or/and the capacity of a heater of the heater unit 36, in the vicinity of the concerned detection element. On the other hand, when lowering the temperature of a certain detection element of the detection element unit 42, the controller 26 adjust the workload of the chip which is mounted on the DAS 24 and located in the vicinity of the concerned detection element or/and the amount of air of the cooling fan 35. Thus, the temperature of a detection element of the detection element unit 42 of the X-ray detector 22 is controlled within a range of, for example, 40±1 [° C.] which is higher than the room temperature by the adjustments of the workload of the chip mounted on the DAS 24, the capacity of the heater unit 36, and the amount of air of the cooling fan 35. It is possible to maintain the image quality of the CT image generated by the image processing system 12 by controlling the temperature of every detection element of the detection element unit 42.

The time chart in the operation of the X-ray CT apparatus 1A of the second embodiment is the same as that in the operation of the X-ray CT apparatus 1 of the first embodiment and, therefore, will be omitted from description.

Figure 7:
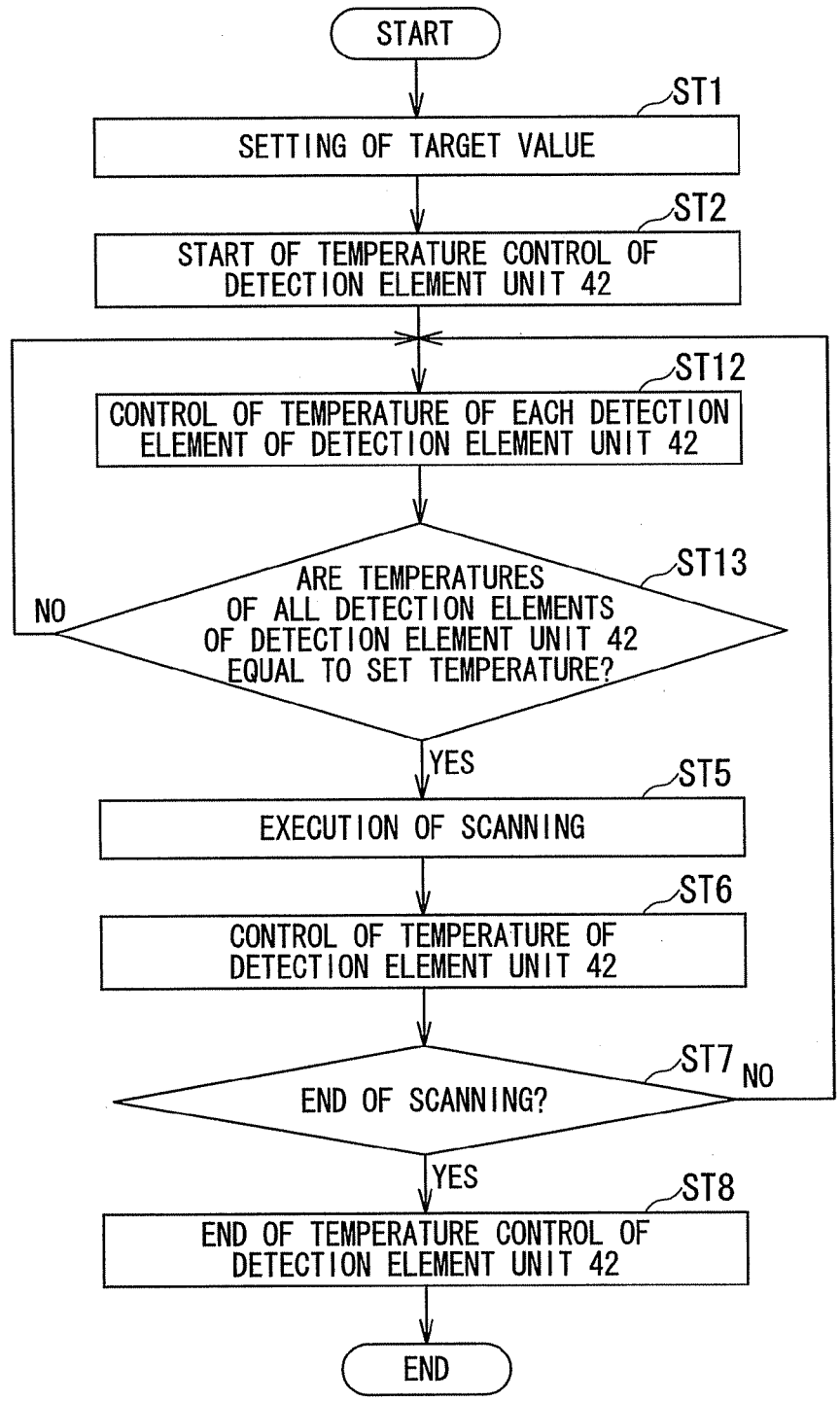
FIG. 7 is a first flowchart showing the operation of the X-ray CT apparatus of the second embodiment.

Next, the operation of the X-ray CT apparatus 1A of the second embodiment will be described by using a first flowchart shown in FIG. 7. It is noted that in the flowchart shown in FIG. 7, the same steps as those of the flowchart shown in FIG. 4 will be given the same reference characters, and their description will be omitted.

In a non-scanning period T1 shown in FIG. 3, the controller 26 repeatedly detects the temperature of the detection element unit 42 with the temperature sensor unit 52a. That is, the controller 26 repeatedly measures the temperature distribution of the detection element unit 42. Then, the controller 26 respectively adjusts the workloads of the plurality of chips that make up the DAS 24, or/and respectively adjusts the capacities of the plurality of heaters of the heater unit 36 based on the temperature distribution of the detection element unit 42 with an appropriate temperature set at step ST1 as the target value. That is, the controller 26 controls the temperature of each detection element of the detection element unit 42 (step ST12). For example, in step ST12, a PID control of the temperature of each detection element of the detection element unit 42 is performed with the power consumption of the chip of the DAS 24 as the manipulated variable.

Next, upon receiving an instruction to start scanning, the controller 26 determines whether or not the temperatures (or a representative temperature such as an average temperature, etc.) of all the detection elements of the detection element unit 42, which are detected by the temperature sensor unit 52a, are equal to the target value set at step ST1 (step ST13). When the determination at step ST13 is YES, that is, it is determined that the temperatures of all the detection elements of the detection element unit 42, which are detected with the temperature sensor unit 52a, are equal to the target value set at step ST1, the controller 26 executes scanning (step ST5). That is, using FIG. 3, the X-ray CT apparatus 1 makes a transition from a non-scanning period T1 to a scanning period T2.

On the other hand, when the determination at step ST13 is NO, that is, it is determined that the temperature of any detection element of the detection element unit 42, which is detected with the temperature sensor unit 52a, is not equal to the target value set at step ST1, the controller 26 controls the temperature of each detection element of the detection element unit 42 until the temperatures of all the detection elements of the detection element unit 42 reach the target value set at step ST1 (step ST12).

Figure 8:
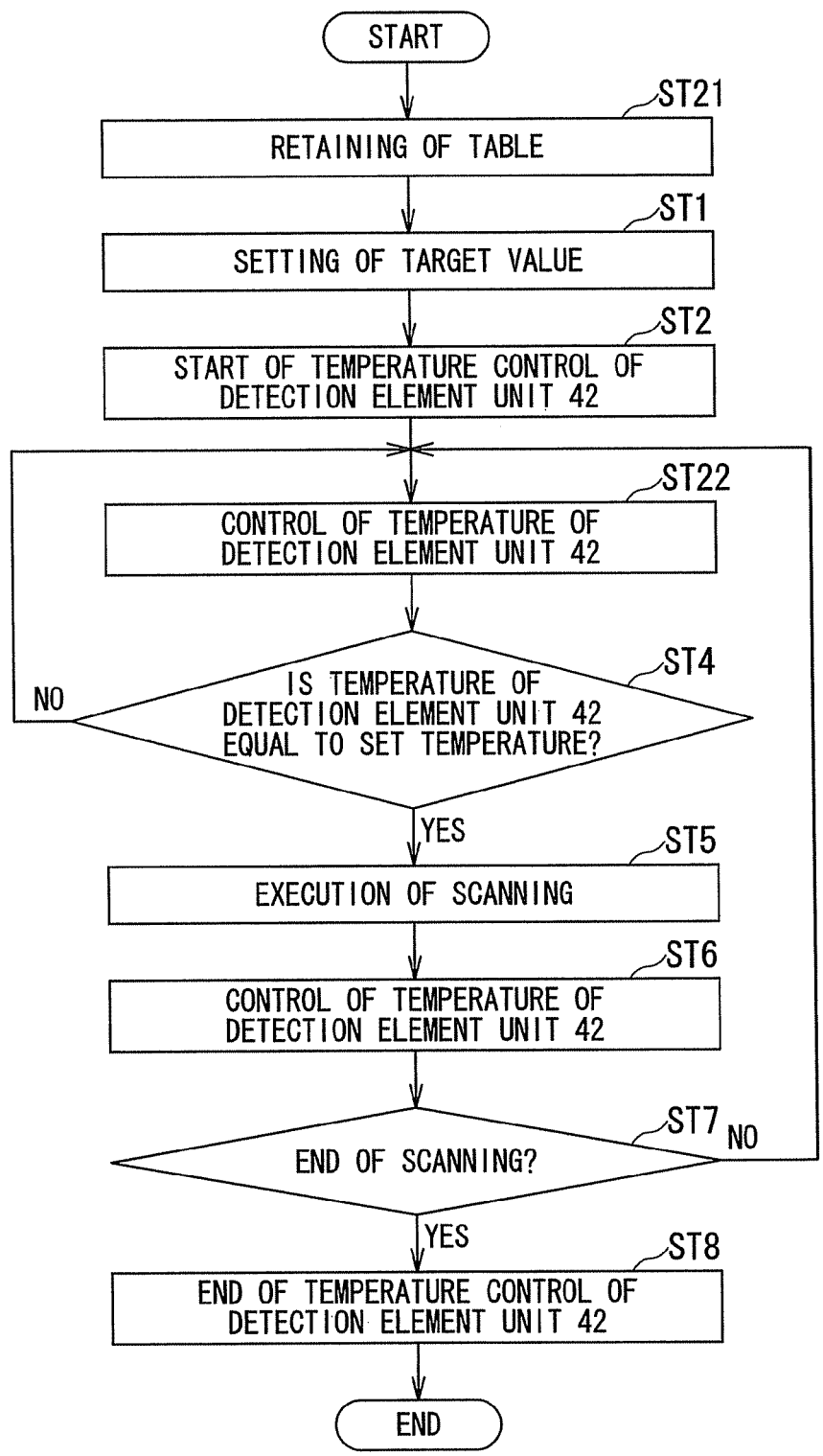
FIG. 8 is a second flowchart showing the operation of the X-ray CT apparatus of the second embodiment.
Figure 9:
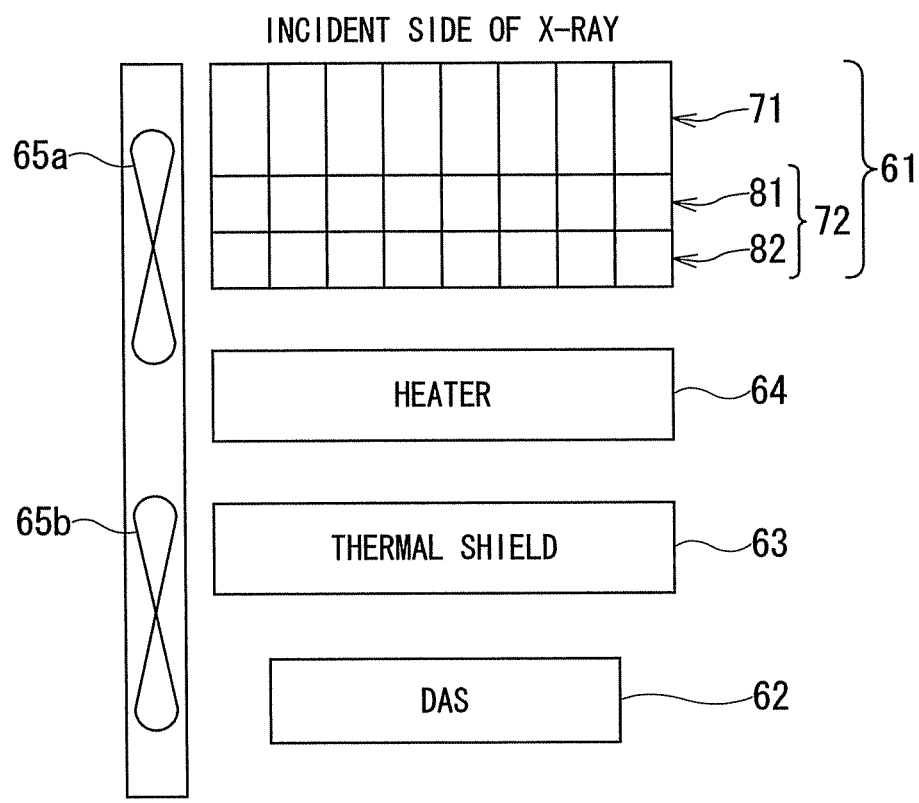
FIG. 9 is a side view showing an outline of a configuration of a periphery of an X-ray detector and a DAS in a conventional X-ray CT apparatus.

Next, the operation of the X-ray CT apparatus 1A of the second embodiment will be described by using a second flowchart shown in FIG. 8. It is noted that in the flowchart shown in FIG. 8, the same steps as those of the flowchart shown in FIG. 4 are given the same reference characters, and their description will be omitted.

First, the controller 26 of the X-ray CT apparatus 1A retains a table which correlates the temperature of the detection element unit 42 with the combination of the workload of the DAS 24 and the capacity of the heater unit 36 (step ST21).

In the non-scanning period T1 shown in FIG. 3, the controller 26 repeatedly detects the temperature of the detection element unit 42 with the temperature sensor unit 52a. When the temperature sensor unit 52a includes a plurality of temperature sensors, a representative value of a plurality of detected temperatures, such as an average value, may be regarded as the temperature of the detection element unit 42. Then, the controller 26 obtains a combination of a workload of the DAS 24 and a capacity of the heater unit 36, corresponding to a detected temperature of the detection element unit 42, from the table. The controller 26 adjusts the workload of the DAS 24 and the capacity of the heater unit 36 according to the obtained combination with an appropriate temperature set at step ST1 as the target value. That is, the controller 26 controls the temperature of the detection element unit 42 (step ST22). For example, in step ST22, a PID control of the temperature of the detection element unit 42 is performed with the power consumption of the DAS 24 as the manipulated variable.

According to the X-ray CT apparatus 1A of the second embodiment, it is possible to facilitate the temperature control of the detection element unit 42 with a simple structure using a heater of a compact structure, thereby improving the image quality of a CT image, and allowing the temperature control to be applied particularly to a case in which the X-ray detector 22 and the DAS 24 are configured to be adjacent structures, or a unitary structure.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
   an X-ray source configured to generate an X-ray;
   an X-ray detector configured to detect the X-ray;
   a temperature sensor configured to detect a temperature of the X-ray detector;
   a data acquisition unit configured to acquire data from the X-ray detector; and
   a controller configured to control a temperature of the X-ray detector through adjustment of a workload of the data acquisition unit during a non-scanning time.

2. The X-ray CT apparatus according to claim 1, further comprising:
   a cooling fan, wherein
   the controller controls the temperature of the X-ray detector through adjustment of an amount of air of the cooling fan during a scanning time.

3. The X-ray CT apparatus according to claim 1, wherein the controller sets a target value of a temperature of the X-ray detector, and controls the temperature of the X-ray detector such that the temperature of the X-ray detector is equal to the target value, during the non-scanning time.

4. The X-ray CT apparatus according to claim 1, wherein the controller controls a temperature of the X-ray detector through adjustment of power consumption of the data acquisition unit by varying an acquisition operation of the data acquisition unit between from 0 to a maximum, during the non-scanning time.

5. The X-ray CT apparatus according to claim 1, wherein the X-ray detector comprises a photodiode, and the temperature sensor is provided in the photodiode.

6. The X-ray CT apparatus according to claim 1, wherein the X-ray detector and the data acquisition unit are configured to be a unitary structure.

7. The X-ray CT apparatus according to claim 1, further comprising:
   a heater configured to heat the X-ray detector, wherein
   the controller controls the temperature of the X-ray detector through adjustment of a workload of the data acquisition unit and a capacity of the heater during the non-scanning time.

8. The X-ray CT apparatus according to claim 7, wherein the controller obtains a combination corresponding to a temperature detected by the temperature sensor based on a table which correlates the temperature of the X-ray detector with the combination of the workload of the data acquisition unit and the capacity of the heater, and adjusts the workload of the data acquisition unit and the capacity of the heater according to the obtained combination.

9. The X-ray CT apparatus according to claim 7, wherein the X-ray detector comprises a plurality of photodiodes which are arranged into a one-dimensional array or a two-dimensional array, and
   a plurality of the heaters are provided in a plane direction of the plurality of photodiodes.

10. The X-ray CT apparatus according to claim 9, wherein a plurality of the temperature sensors are provided in the plane direction of the plurality of photodiodes, and
    the controller adjusts the workload of the data acquisition unit for every chip making up the data acquisition unit and adjusts the capacity of the plurality of heaters for every heater of the plurality of heaters, according to a temperature distribution of the X-ray detector based on a plurality of temperatures detected by the plurality of temperature sensors.

11. The X-ray CT apparatus according to claim 7, wherein the heater is provided within the X-ray detector, and
    the X-ray detector and the data acquisition unit are configured to be a unitary structure.

12. A control method for an X-ray CT apparatus which has: an X-ray source configured to generate an X-ray; an X-ray detector configured to detect the X-ray; a temperature sensor configured to detect a temperature of the X-ray detector; and a data acquisition unit configured to acquire data from the X-ray detector, comprising:
    a controlling step that controls a temperature of the X-ray detector through adjustment of a workload of the data acquisition unit during a non-scanning time.

13. The control method according to claim 12, wherein the control step obtains a combination corresponding to a temperature detected by the temperature sensor based on a table which correlates the temperature of the X-ray detector with the combination of the workload of the data acquisition unit and the capacity of the heater, and adjusts the workload of the data acquisition unit and the capacity of the heater according to the obtained combination.

* * * * *